US010071060B2

(12) United States Patent
Kim

(10) Patent No.: US 10,071,060 B2
(45) Date of Patent: Sep. 11, 2018

(54) ASYMMETRICALLY COATED TABLE

(75) Inventor: Cherng-ju Kim, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 1428 days.

(21) Appl. No.: 11/443,666

(22) Filed: May 30, 2006

(65) Prior Publication Data

US 2007/0009599 A1 Jan. 11, 2007

(51) Int. Cl.
*A61K 9/24* (2006.01)
*A61K 9/28* (2006.01)
*A61K 9/20* (2006.01)

(52) U.S. Cl.
CPC ............... *A61K 9/28* (2013.01); *A61K 9/209* (2013.01); *A61K 9/2886* (2013.01); *A61K 9/2893* (2013.01); *A61K 9/2072* (2013.01)

(58) Field of Classification Search
CPC ...... A61K 9/16; A61K 9/1605; A61K 9/2095; A61K 9/2072; A61K 9/28; A61K 9/209; A61K 9/2893
USPC ................................................ 424/473–485
See application file for complete search history.

(56) References Cited

U.S. PATENT DOCUMENTS

| | | | |
|---|---|---|---|
| 2,714,084 A | 10/1954 | Hermelin | |
| 2,993,837 A | 7/1961 | Millar | |
| 4,361,545 A | 11/1982 | Powell et al. | |
| 4,606,909 A | 8/1986 | Bechgaard et al. | |
| 4,775,536 A | 10/1988 | Patell | |
| 5,162,117 A | 11/1992 | Stupak et al. | |
| 5,213,808 A * | 5/1993 | Bar-Shalom et al. | 424/473 |
| 5,422,123 A * | 6/1995 | Conte | A61K 9/2086 424/479 |
| 5,431,920 A | 7/1995 | Bechard | |
| 5,783,212 A | 7/1998 | Fassihi et al. | |
| 5,817,338 A | 10/1998 | Bergstrand et al. | |
| 5,945,125 A | 8/1999 | Kim | |
| 5,962,024 A | 10/1999 | Marvola et al. | |
| 6,068,859 A | 5/2000 | Curatolo et al. | |
| 6,110,500 A | 8/2000 | Kim | |
| 6,294,200 B1 * | 9/2001 | Conte | A61K 9/209 424/464 |
| 6,303,144 B1 * | 10/2001 | Omura | 424/457 |
| 7,713,549 B2 | 5/2010 | Kim | |
| 2003/0039691 A1 | 2/2003 | Waterman | |
| 2005/0025829 A1 | 2/2005 | Kim | |
| 2008/0003287 A1 | 1/2008 | Kim | |

FOREIGN PATENT DOCUMENTS

| | | | |
|---|---|---|---|
| EP | 0259219 | 3/1988 | |
| EP | 0788790 | 8/1997 | |
| EP | 1053752 | 11/2000 | |
| GB | 1346609 | * 2/1974 | |
| GB | 1346609 A | * 2/1974 | ............. A61K 9/209 |
| WO | WO99/48481 | 9/1999 | |

OTHER PUBLICATIONS

International Search Search Report and Written Opinion of International Searching Authority, PCT/US06/26432, dated Jan. 29, 2007.
International Preliminary Report on Patentability, PCT/US2006/020976, dated Jan. 17, 2008.
Kim, Cherng-Ju, Compressed Donut-Shaped Tablets with Zero-Order Kinetics, Pharmaceutical Research, vol. 12, No. 7, 1995, pp. 1045-1048.
Kim, Cherng-Ju, Release kinetics of coated, donut-shaped tablets for water soluble drugs, European Journal of Pharmaceutical Sciences, 7, 1999, pp. 237-242.
U.S. Appl. No. 11/479,844, Kim, C.
International Search Report and Written Opinion, International Patent Application No. PCT/US06/20976, dated Oct. 5, 2006.
Geranen, Michael, Declaration Under 37 CFR 1.132, Oct. 26, 2010.
Extended European Search Report, EPO Appl. No. 06774554.7, dated Jun. 29, 2012, 7 pages.
Vandelli, M., et al., Selective Coating of Cylindrical Matrices with a Central Hole, International Journal of Pharmaceutics 100, pp. 107-114, 1993.
Sangalli, M., et al., Inert Monolithic Device with a Central Hole for Constant Drug Release, Eur. J. Pharm. Biopharm. 40, No. 6, pp. 370-373, 1994.
International Preliminary Report on Patentability, PCT/US2006/026432, dated Jan. 15, 2009, 6 pages.
Office Action, State Intellectual Property Office, Chinese National Phase of PCT/US2006/026432, dated Aug. 4, 2010, 6 pages.
Supplementary European Search Report, EP Application No. 06771637.3, Search Completed Aug. 7, 2012, 5 pages.
Office Letter and Search Report, Taiwan Intellectual Property Office, Taiwanese Pat. Appl. No. 095124301, dated Mar. 5, 2012.
Decision of Rejection, Taiwan Intellectual Property Office, Taiwanese Pat. Appl. No. 095124301, dated Oct. 8, 2012 (translation).
Communication, European Patent Office, European Pat. Appl. 06771637.3, dated Aug. 21, 2015.

\* cited by examiner

*Primary Examiner* — Micah Paul Young
(74) *Attorney, Agent, or Firm* — Richard Blakely Glasgow

(57) ABSTRACT

A tablet for the controlled release of a drug. The tablet is in the form of an asymmetrically coated tablet so that immediate release or time-delayed release times can be precisely controlled and the extended release slab may provide zero-order or first-order extended release and pulsatile release depending on the excipients used in the tablet formulations. The core of the tablet is coated with an asymmetrical coating, that is, a coating with regions having different properties. The coatings may include drugs in varying concentrations. Further, different regions of the coating may have different rates of dissolution. The core of the tablet may be provided with a constant cross-sectional area along a longitudinal length of the tablet, a coating having a first region with a more rapid rate of dissolution than a second region. The dissolution of the first region exposes only the cross-sectional area to the dissolution medium. The second region of the coating prevents any other portion of the core of the tablet from being exposed to the dissolution medium. Therefore, since the cross-sectional area remains constant as it is dissolved, the rate of release of the drug from the core of the tablet remains constant. The cross-sectional area may be of any geometrical configuration so long as the area remains constant as the core dissolves.

14 Claims, 8 Drawing Sheets

ASYMMETRICALLY COATED TABLE

CROSS-REFERENCE TO RELATED APPLICATIONS

This application claims the benefit of U.S. Provisional Application No. 60/697,743 filed Jul. 8, 2005, the disclosure of which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to pharmaceutical dosage forms and in, particular, to a tablet containing a drug having a precisely predetermined release kinetics.

2. Brief Description of the Related Art

There have been various attempts made to create extended release dosage forms for orally administering drugs. Some dosage forms tend to release the drug at rates that do not correlate well with the needs of the patient. For example, a particular dosage form may release a large amount of the drug rapidly upon ingestion where a more constant rate of release is desirable. In other situations, varying release rates may be desirable. Additional background information on the art of controlling release rates of drugs in orally administered dosage forms is found in U.S. Pat. Nos. 5,945,125 and 6,110,500 and U.S. Published Patent Application No. US2005/0025829, the disclosures of which are incorporated herein by reference. Dosage forms typically comprise the drug; that is, the pharmaceutically active substance, dispersed in various excipients including polymers whose rates of dissolution are known. As the tablet is dissolved, the drug is released at a predicted rate. Coating excipients having various rates of dissolution have also been used for time delayed release of drugs.

Common oral extended release or pulsatile release dosage forms include tablets, caplets, and capsules containing small spherical pellets. Such dosage forms typically have the combined geometry of slabs and cylinders, which tend to produce varying release rates. As the tablet is dissolved, the amount of surface area exposed to the dissolution medium changes, thereby changing the rate at which the dissolution occurs and thus the rate of release of the drug. In certain situations, it is desirable that the rate of release of drugs has a zero-order kinetics; that is, the drug is released at a constant or nearly constant rate. However, the rate of drug release from conventional dosage forms typically does not follow zero-order kinetics and thus the drug release rate decreases as release time progresses.

While constant drug release rates are desirable in certain circumstances, it is more generally desirable to be able to customize the kinetics of drug release. For example, a rapid initial release (a burst) may desirably be followed by a period of constant release. In other examples, it might be desirable to delay the release of the drug for a period of time or to release a pulse of the drug after a period of constant release.

As noted above, in order to obtain immediate release followed by extended release or time-delayed release followed by extended release or time-delayed release followed by pulsatile release, dosage forms are coated uniformly with appropriate coating excipients with or without drugs dispersed in the coating. Once the coating layer disappears (or dissolves), the extended release tablet shape is exposed to the dissolution medium and thus the same kinetic problems of other dosage forms are encountered.

These and other problems of the prior art are addressed by the present invention as described following.

BRIEF SUMMARY OF THE INVENTION

The present invention uses asymmetrically coated tablets so that immediate release or time-delayed release times can be precisely controlled and the extended release tablet may provide zero-order or first-order extended release and pulsatile release depending on the excipients used in the tablet formulations. Immediate release or time-delayed release time can be precisely determined. Extended release kinetics can be manipulated as a dosage form designer wishes.

The core of the tablet in the present invention is coated with an asymmetrical coating, that is a coating with regions having different properties. The coatings may include drugs in varying concentrations. Further, different regions of the coating may have different rates of dissolution. In one embodiment of the present invention, the core of the tablet is provided with a constant cross-sectional area along a longitudinal length of the tablet. So long as only the cross-sectional area is exposed to the dissolution medium, zero-order kinetics; i.e., a constant release rate, may be achieved. This is accomplished by providing the tablet with a coating having a first region with a more rapid rate of dissolution than a second region. The dissolution of the first region exposes only the cross-sectional area to the dissolution medium. The second region of the coating prevents any other portion of the core of the tablet from being exposed to the dissolution medium, at least until the core of the tablet is dissolved. Therefore, since the cross-sectional area remains constant as it is dissolved, the rate of release of the drug from the core of the tablet remains constant. The cross-sectional area may be of any geometrical configuration so long as the area remains constant as the core dissolves.

BRIEF DESCRIPTION OF THE DRAWINGS

FIG. 7A shows the tablet with two coating regions, a first region comprising a water soluble polymer and a second region comprising a water insoluble polymer. In alternative embodiments, the first region may comprise a water soluble polymer and the second region a water soluble polymer, where the first region has a greater rate of dissolution than the second region. The first region incorporates a drug so that the rapid dissolution of the first region as shown in FIG. 7B provides a burst release of the drug as shown by the non-zero fractional release at time=0 in the graph of FIG. 1. With the dissolution of the first region, the drug-containing core is exposed to the dissolution medium and the drug begins to be released at a constant rate as shown by the essentially linear portion of the fractional release curve of FIG. 1 until the core is completely dissolved as shown in FIG. 7C.

FIG. 8A shows the tablet with two coating regions, a first region comprising a water soluble polymer and a second region comprising a water insoluble polymer. In alternative embodiments, the first region may comprise a water soluble polymer and the second region a water-soluble polymer, where the first region has a greater rate of dissolution than the second region. The rate of dissolution of the first region is selected so that the release of the drug from the core is delayed for an interval of time as shown in the time axis of FIG. 2. With the dissolution of the first region as shown in FIG. 8B, the core is exposed to dissolution and the drug begins to be released at a constant rate as shown by the essentially linear portion of the fractional release curve of FIG. 2 until completely dissolved as shown in FIG. 8C.

FIG. 9A shows the tablet with two coating regions, a first region comprising a water soluble polymer and a second region comprising a water insoluble polymer. In alternative embodiments, the first region may comprise a water soluble polymer and the second region a water soluble polymer, where the first region has a greater rate of dissolution than the second region. The rate of dissolution of the first region is selected so that the release of the drug from the core tablet is delayed for an interval of time as shown in the time axis of FIG. 3. The delay is greater than the delay of the embodiment shown in FIG. 2. The greater delay can be achieved by selecting the coating material or by a greater thickness. With the dissolution of the first region as shown in FIG. 9B, the core is exposed to the dissolution media and begins to be released at a constant rate as shown by the essentially linear portion of the fractional release curve of FIG. 3 until completely dissolved as shown in FIG. 9C.

FIG. 10A shows the tablet with two coating regions, a first region comprising a water soluble polymer and a second region comprising a water insoluble polymer. In alternative embodiments, the first region may comprise a water soluble polymer and the second region a water soluble polymer, where the first region has a greater rate of dissolution than the second region. The rate of dissolution of the first region as shown in FIG. 10B is selected so that no appreciable delay occurs in the release of the drug from the first part of the core tablet. The release of the drug from the first part of the core tablet is shown by the initial steep linear rise in the fractional release as shown in FIG. 4. This time period corresponds to the situation illustrated in FIG. 10B. When the first part of the core has been completely dissolved, the second part begins to dissolve (FIG. 10C) at a less rapid but still essentially linear rate as shown by the less steeply pitched part of the curve of FIG. 4 until the drug from the second part is completely dissolved as shown in FIG. 10D.

DETAILED DESCRIPTION OF THE INVENTION

The preferred embodiments of the invention are described herein with reference to FIG. 1-12C.

Figure 1:
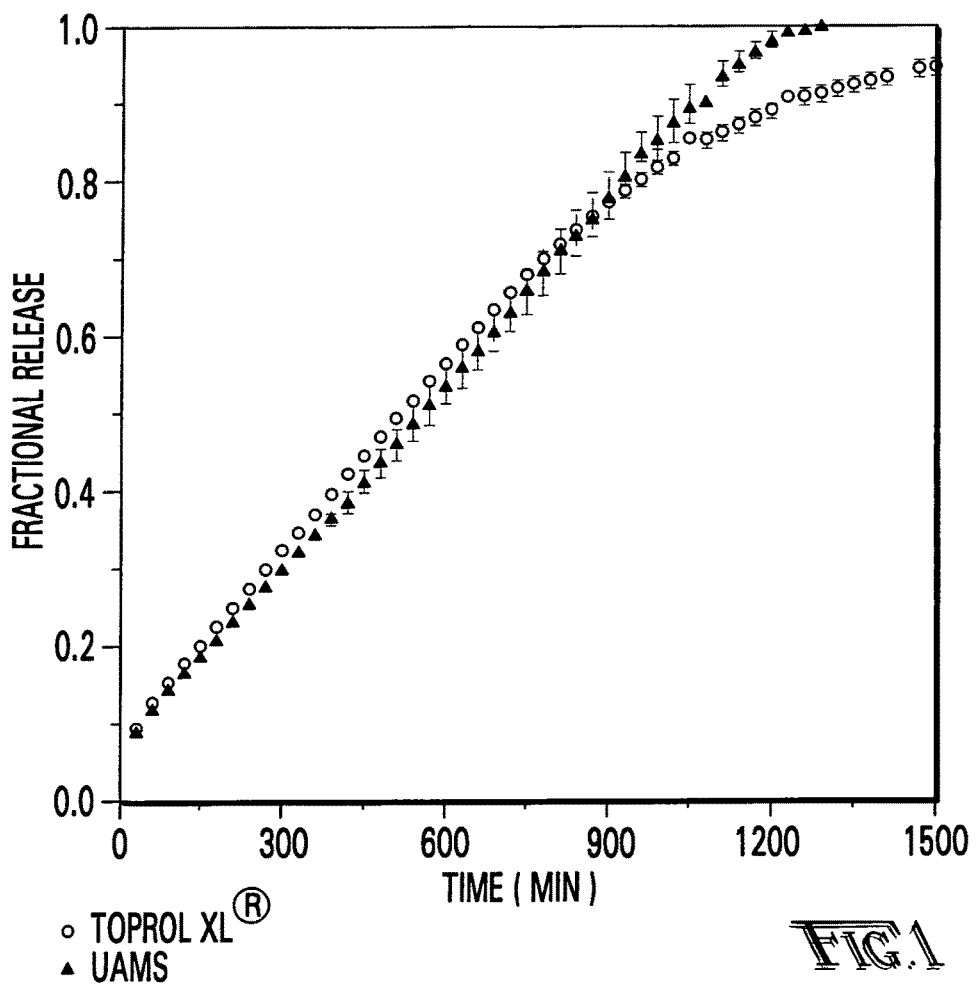
FIG. 1 is a graph of the release rate of a drug from an asymmetrically coated table of the present invention superimposed on a graph of the release rate of a commercially-available brand of anti-hypertensive pharmaceutical, Toprol XL® (Astrazeneca LP, Wayne, Pa. USA).

A first embodiment of the present invention is described with respect to FIG. 1 and FIGS. 7A-C. FIG. 1 is a graph of the release rate of a drug from an asymmetrically coated table 10 of the present invention superimposed for comparison on a graph of the release rate of a commercially available brand of pharmaceutical, Toprol XL®. FIG. 1 thus illustrates how the tablet 10 of the present invention may be formed to match a specific release rate of a known commercially-available product. The tablet 10 comprises a core 11 having a drug dispersed in various excipients including polymers as known in the art to allow the core 11 to dissolve at a predicted rate and therefore provide an extended release of the drug.

Figure 7A:
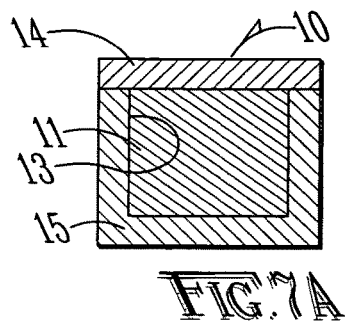
FIGS. 7A-C are elevation sectional views of a first embodiment of the asymmetrically coated table of the present invention. The core of the tablet has a cross-sectional area that is constant along a longitudinal length of the core. This area may be of any geometrical configuration so long as the area remains constant as the core dissolves. This ensures a constant release rate; i.e., zero-order kinetics.
Figure 7B:
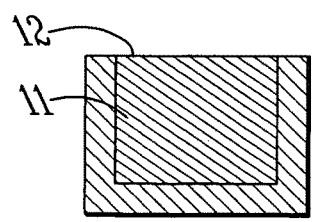
Figure 7C:
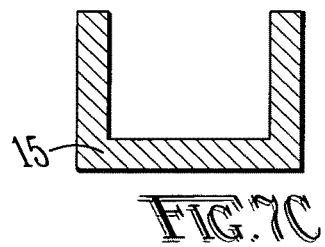

FIGS. 7A-C are elevation sectional views of the first embodiment where the core 11 of the tablet 10 has a cross-sectional area 12 that is constant along a longitudinal length 13 of the tablet 10. This area 12 may be of any geometrical configuration so long as the area 12 remains constant as the core 11 dissolves. This ensures a constant release rate; i.e., zero-order kinetics. FIG. 7A shows the tablet 10 with two coating regions, a first region 14 comprising a water soluble polymer and a second region 15 comprising a water insoluble polymer. Alternatively, the first region 14 may comprise a water soluble polymer and the second region 15 may also comprise a water soluble polymer, where the first region 14 has a greater rate of dissolution than the second region 15. The first region 14 covers only the cross-sectional area 12 and therefore only the cross-sectional area 12 is exposed to the dissolution medium following the dissolution of the first region 14. The second region 15 does not dissolve or has a delayed dissolution so that no other part of the core 11 is exposed to the dissolution medium at least until the core 11 is completely dissolved. In this embodiment, the first region 14 of the coating incorporates a drug so that the rapid dissolution of the first region 14 as shown in FIG. 7B provides a burst release of the drug as shown by the non-zero fractional release at time=0 in the graph of FIG. 1. With the dissolution of the first region 14, the core is exposed to the dissolution medium and the drug begins to be released at a constant rate as shown by the essentially linear portion of the fractional release curve of FIG. 1. Various means are known in the art to effect different rates of release of a drug from a coating material, including using dissolving and non-dissolving but permeable materials.

Figure 2:
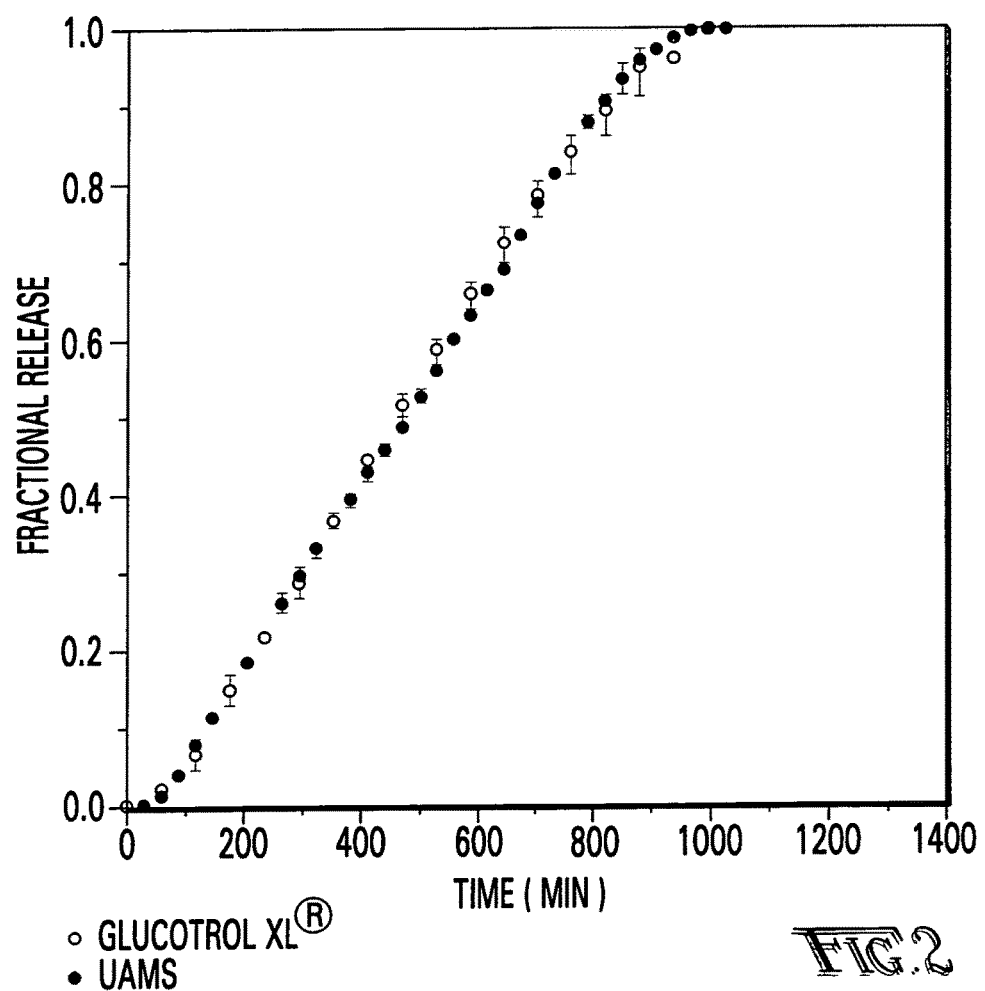
FIG. 2 is a graph of the release rate of a drug from a second embodiment of the asymmetrically coated table of the present invention superimposed on a graph of the release rate of a commercially-available brand of antidiabetic preparation, Glucotrol XL® (Pfizer Inc., New York, N.Y. USA).

A second embodiment of the present invention is described with respect to FIG. 2 and FIGS. 8A-C. FIG. 2 is a graph of the release rate of a drug from a second embodiment of the asymmetrically coated table 10 of the present invention superimposed on a graph of the release rate of a commercially-available brand of pharmaceutical, Glucotrol XL®.

Figure 8A:
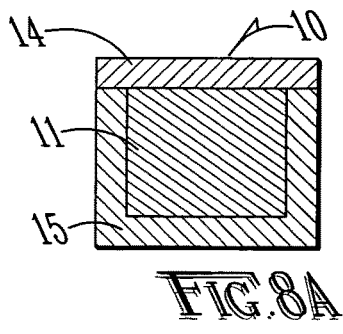
FIGS. 8A-C are elevation sectional views of a second embodiment of the asymmetrically coated table of the present invention. The core of the tablet has a cross-sectional area that is constant along a longitudinal length of the core. This area may be of any geometrical configuration so long as the area remains constant as the core dissolves. This ensures a constant release rate; i.e., zero-order kinetics.
Figure 8B:
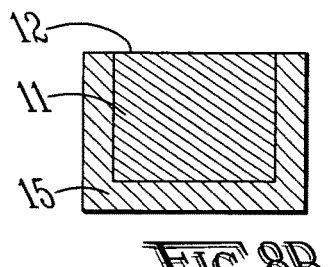
Figure 8C:
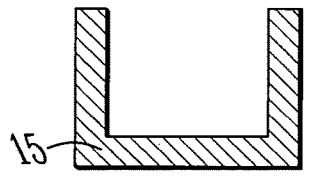

FIGS. 8A-C are elevation sectional views of the second embodiment of the asymmetrically coated table 10 of the present invention. As with the first embodiment, the core 11 of the tablet 10 has a cross-sectional area 12 that is constant along a longitudinal length of the core 11. This area 12 may be of any geometrical configuration so long as the area 12 remains constant as the core 11 dissolves. This ensures a constant release rate; i.e., zero-order kinetics. FIG. 8A shows the tablet 10 with two coating regions, a first region 14 comprising a water soluble polymer and a second region 15 comprising a water insoluble polymer. Alternatively, the first region 14 may comprise a water soluble polymer and the second region 15 may also comprise a water soluble polymer, where the first region 14 has a greater rate of dissolution than the second region 15. The rate of dissolution of the first region 14 is selected so that the release of the drug from the core 11 is delayed for an interval of time as shown in the time axis of FIG. 2. As known in the art, the delay may be determined by the thickness of the first region 12 or by selecting water-soluble polymers for the first region 12 having greater or lesser molecular weights. Higher molecular weight polymers dissolve more slowly than lower molecular weight polymers. With the dissolution of the first region 14, the core 11 is exposed to dissolution and the drug begins to be released at a constant rate as shown by the essentially linear portion of the fractional release curve of FIG. 2.

Figure 3:
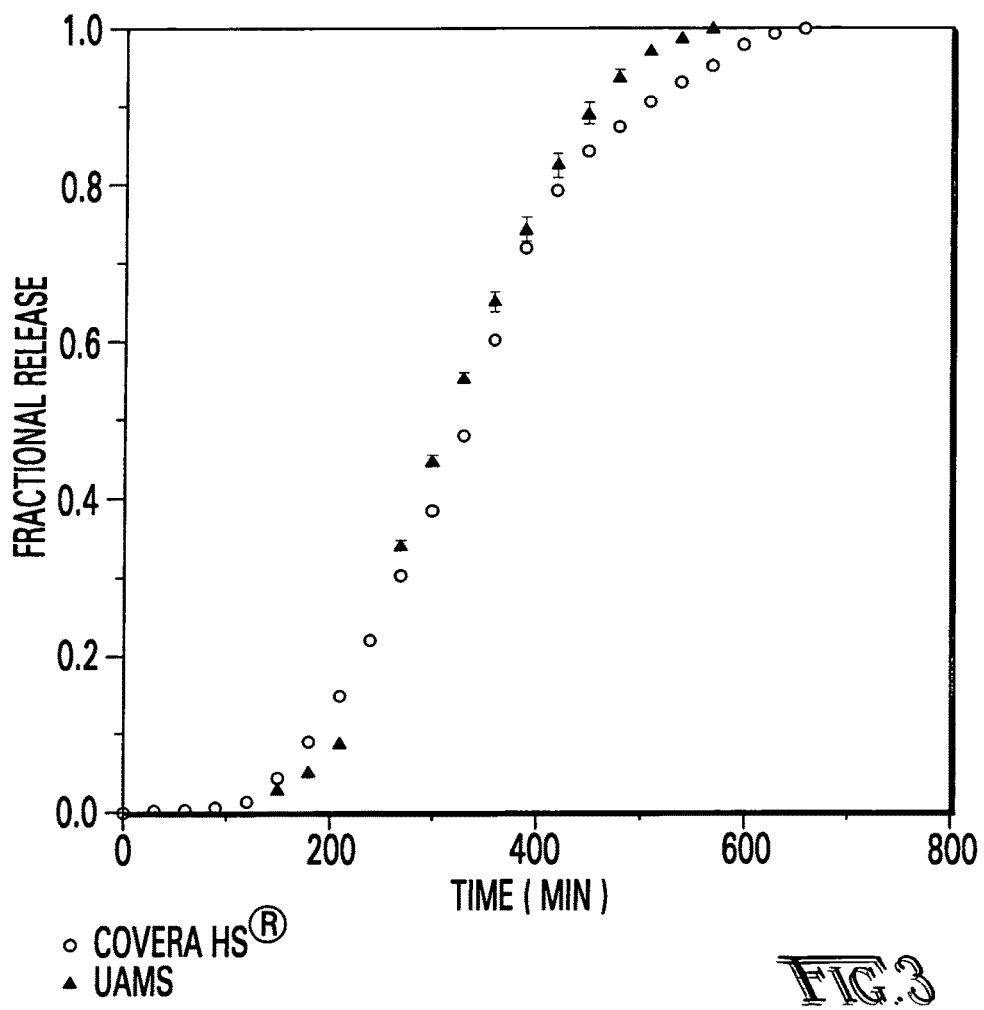
FIG. 3 is a graph of the release rate of a drug from a third embodiment of the asymmetrically coated table of the present invention superimposed on a graph of the release rate of a commercially-available brand of pharmaceutical for the treatment of cardiovascular conditions, Covera HS® (G.D. Searle LLC, North Peapack, N.J. USA).

A third embodiment of the present invention is described with respect to FIG. 3 and FIGS. 9A-C. FIG. 3 is a graph of the release rate of a drug from a third embodiment of the asymmetrically coated table 10 of the present invention superimposed on a graph of the release rate of a commercially available brand of pharmaceutical, Covera HS®.

Figure 9A:
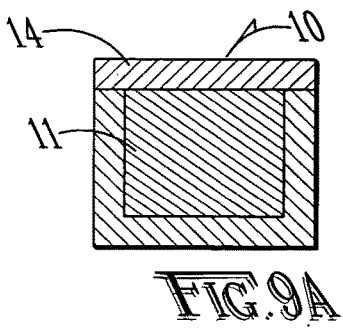
FIGS. 9A-C are elevation sectional views of a third embodiment of the asymmetrically coated table of the present invention. The core of the tablet has a constant cross-sectional area along a longitudinal length of the core. This area may be of any geometrical configuration so long as the area remains constant as the core dissolves. This ensures a constant release rate; i.e., zero-order kinetics.
Figure 9B:
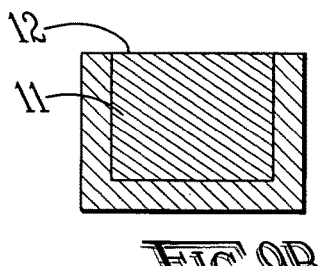
Figure 9C:
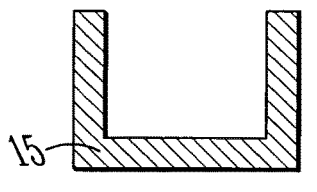

FIGS. 9A-C are elevation sectional views of a third embodiment of the asymmetrically coated table 10 of the present invention. As with the previous embodiments, the core 11 of the tablet 10 has a cross-sectional area 12 that is constant along a longitudinal length of the core 11. This area 12 may be of any geometrical configuration so long as the area 12 remains constant as the core 11 dissolves. This ensures a constant release rate; i.e., zero-order kinetics. FIG. 9A shows the tablet 10 with two coating regions, a first region 14 comprising a water soluble polymer and a second region 15 comprising a water insoluble polymer. Alternatively, the first region 14 may comprise a water soluble polymer and the second region 15 may also comprise a water soluble polymer, where the first region 14 has a greater rate of dissolution than the second region 15. The rate of dissolution of the first region 14 is selected so that the release of the drug from the core 11 is delayed for an interval of time as shown in the time axis of FIG. 3. The delay is greater than the delay of the embodiment shown in FIG. 2. The greater delay can be achieved as described by selecting a higher molecular weight polymer for the coating material or by selecting a greater thickness. With the dissolution of the first region 14, the core 11 is exposed to the dissolution media and the drug begins to be released at a constant rate as shown by the essentially linear portion of the fractional release curve of FIG. 3.

Figure 4:
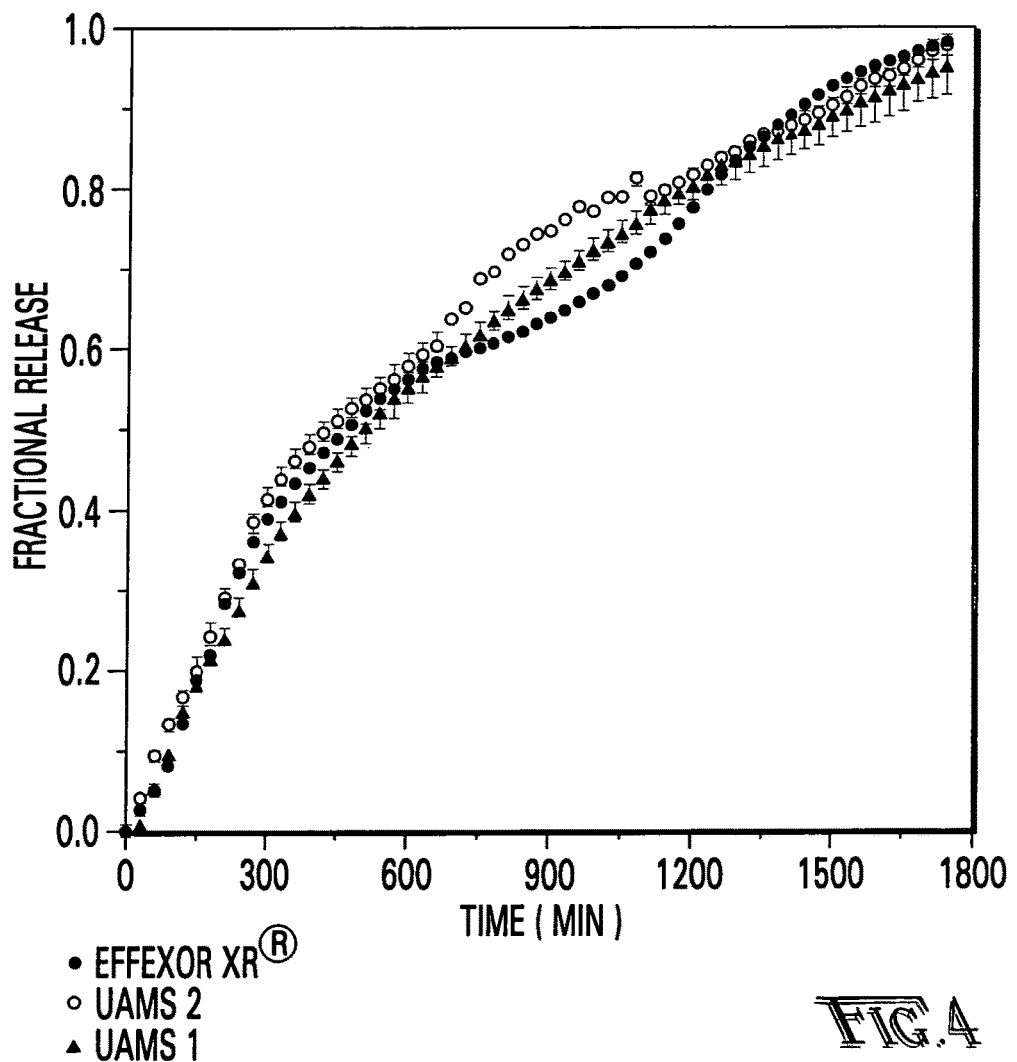
FIG. 4 is a graph of the release rate of a drug from a fourth embodiment of the asymmetrically coated table of the present invention superimposed on a graph of the release rate of a commercially-available brand of antidepressant pharmaceutical, Effexor XR® (Wyeth, Madison, N.J. USA).

A fourth embodiment of the present invention is described with respect to FIG. 4 and FIGS. 10A-D. FIG. 4 is a graph of the release rate of a drug from a fourth embodiment of the asymmetrically coated tablet 10 of the present invention superimposed on a graph of the release rate of a commercially-available brand of pharmaceutical, Effexor XR®.

Figure 10A:
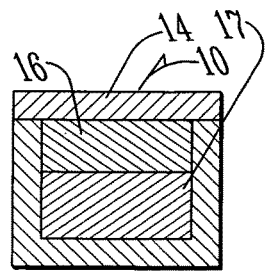
FIGS. 10A-D are elevation sectional views of a fourth embodiment of the asymmetrically coated table of the present invention. The core of the tablet has a constant cross-sectional area along a longitudinal length of the core. This area may be of any geometrical configuration so long as the area remains constant as the drug dissolves. This ensures a constant release rate; i.e., zero-order kinetics. However, unlike the embodiments described above, the embodiment of FIGS. 10A-D has a core formed in two parts. The two parts are formulated to give two different release rates. The rate from the first part is set to be greater than the release rate from the second part. As in the previous embodiments.
Figure 10B:
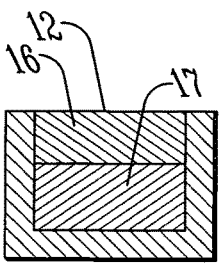
Figure 10C:
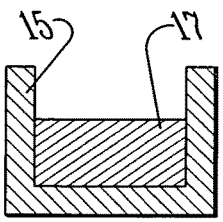
Figure 10D:
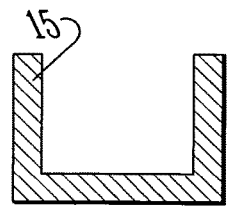

FIGS. 10A-D are elevation sectional views of the fourth embodiment of the asymmetrically coated tablet 10 of the present invention. The core 11 of the tablet 10 has a constant cross-sectional area 12 as described previously. However, unlike the embodiments described above, the embodiment of FIGS. 10A-D has a core 11 formed in two parts. The two parts are formulated to give two different release rates for the drug. In this example, the rate from the first part 16 is set to be greater than the release rate from the second part 17; however, the present invention contemplates that either part may have greater release rates than the other. Further, any number of parts may be employed as a particular situation requires. As in the previous embodiments, FIG. 10A shows the tablet 10 with two coating regions, a first region 14 comprising a water soluble polymer and a second region 15 comprising a water insoluble polymer. Alternatively, the first region 14 may comprise a water soluble polymer and the second region 15 a water soluble polymer, where the first region 14 has a greater rate of dissolution than the second region 15. In this example, the rate of dissolution of the first region 14 is selected so that no appreciable delay occurs in the release of the drug from the first part 16 of the core 11. The release of the drug from the first part of the core 11 is shown by the initial steep linear rise in the fractional release as shown in FIG. 4. This time period corresponds to the situation illustrated in FIG. 10B. When the first part 16 of the core 11 has been completely dissolved, the second part 17 begins to dissolve (FIG. 10C) at a less rapid but still essentially linear rate as shown by the less steeply pitched part of the curve of FIG. 4 until the drug from the second part 17 is completely dissolved as shown in FIG. 10D. Different release rates of the drug may be accomplished by different initial concentrations of the drug in each part 16, 17 or by varying the excipients as known in the art.

Figure 5:
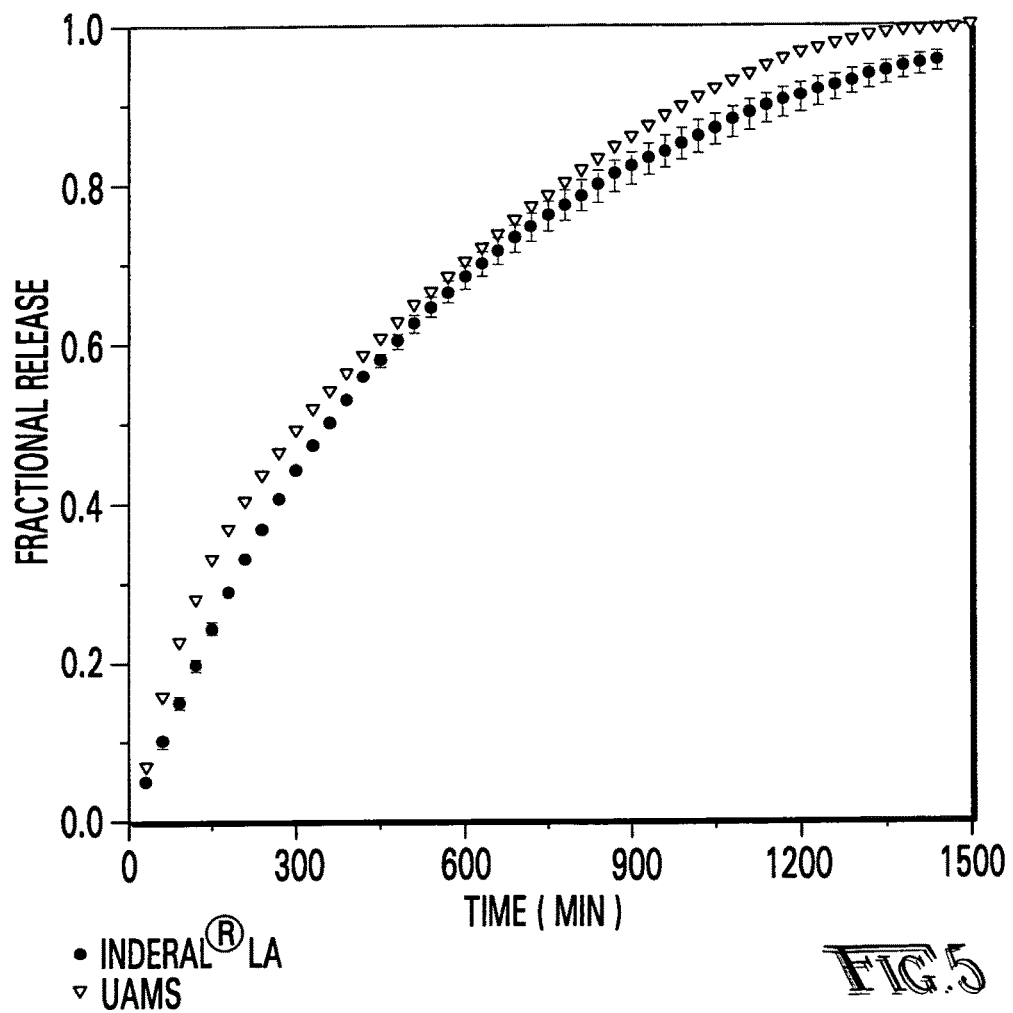
FIG. 5 is a graph of the release rate of a drug from a fifth embodiment of the asymmetrically coated table of the present invention superimposed on a graph of the release rate of a commercially-available brand of adrenergic beta-receptor blocking agent, Inderal® LA (Wyeth, Madison, N.J. USA).

A fifth embodiment of the present invention is described with respect to FIG. 5 and FIGS. 11A-C. FIG. 5 is a graph of the release rate of a drug from the fifth embodiment of the asymmetrically coated table of the present invention superimposed on a graph of the release rate of a commercially-available brand of pharmaceutical, Inderal® LA.

Figure 11A:
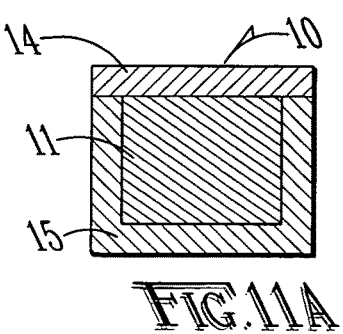
FIGS. 11A-C are elevation sectional views of a fifth embodiment of the asymmetrically coated table of the present invention. This embodiment is similar to the embodiments of FIGS. 1-4 and 6 where the first coating dissolves as shown in FIG. 11B, but in this embodiment the core of the tablet is made with a water insoluble polymer rather than the water soluble polymers of FIGS. 1-4 and 6. By the use of water insoluble polymers, the drug release as shown in FIG. 11C is determined by Fickian kinetics according to the graph of FIG. 5.
Figure 11B:
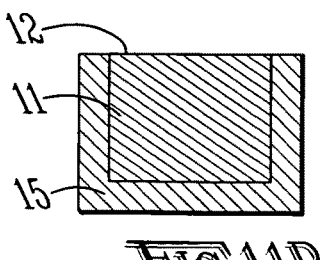
Figure 11C:
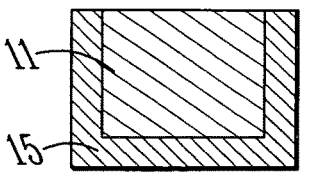

FIGS. 11A-C are elevation sectional views of the fifth embodiment of the asymmetrically coated tablet 10 of the present invention. This embodiment is similar to the embodiments of FIGS. 1-4 and 6, but the core 11 of the tablet 10 is made with a water-insoluble polymer rather than the water-soluble polymers of FIGS. 1-4 and 6. By the use of water-insoluble polymers, the rate of the drug release is determined by Fickian kinetics as known in the art and as shown in FIG. 5.

Figure 6:
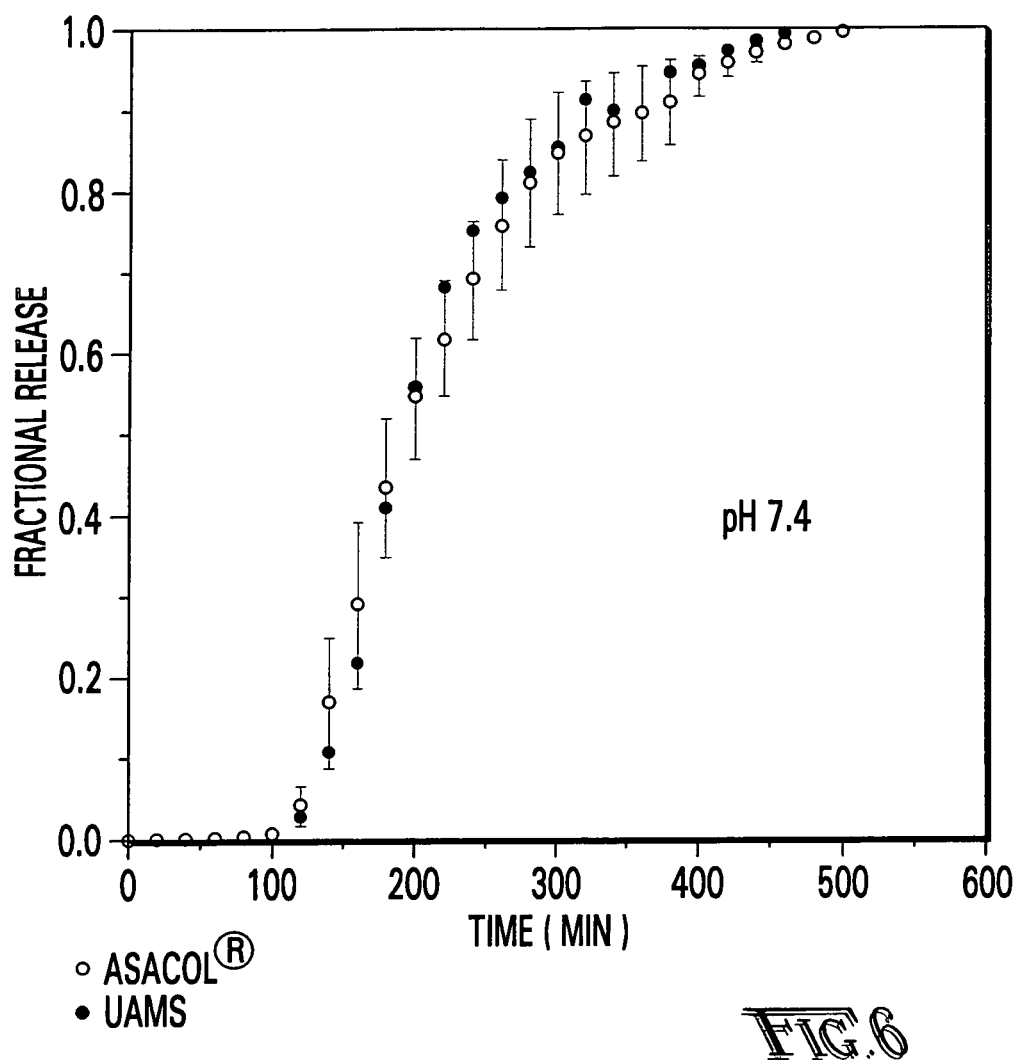
FIG. 6 is a graph of the release rate of a drug from a sixth embodiment of the asymmetrically coated table of the present invention superimposed on a graph of the release rate of a commercially-available brand of pharmaceutical for the treatment of digestive tract disorders, Asacol® (Medeva Pharma Schweiz AG, Liestal, Switzerland).

A sixth embodiment of the present invention is described with respect to FIG. 6 and FIGS. 12A-C. FIG. 6 is a graph of the release rate of a drug from the sixth embodiment of the asymmetrically coated tablet 10 of the present invention superimposed on a graph of the release rate of a commercially-available brand of pharmaceutical, Asacol®.

Figure 12A:
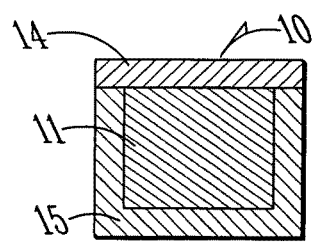
FIGS. 12A-C are elevation sectional views of a sixth embodiment of the asymmetrically coated table of the present invention. In this embodiment as shown in FIG. 12A, the first coating region is made of an enteric polymer which is soluble at an enteric pH of 5.0 and higher. Depending on the thickness of the polymer, the dissolution of the first region is delayed until the tablet has been exposed to an enteric pH for a given period of time. After dissolution of the first region as shown in FIG. 12B, the core dissolves as shown in FIGS. 6 and 12C.
Figure 12B:
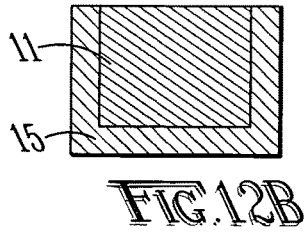
Figure 12C:
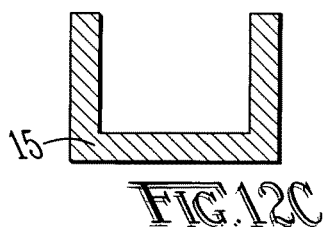

FIGS. 12A-C are elevation sectional views of the sixth embodiment of the asymmetrically coated tablet 10 of the present invention. In this embodiment, the first coating region 14 is made of an enteric polymer which is soluble at an enteric pH of 5.0 and higher. Depending on the thickness of the polymer in the first region 14, the dissolution of the first region 14 is delayed until the tablet 10 has been exposed to an enteric pH for a given period of time. After dissolution of the first region 14, the core 11 dissolves at the rate shown in FIG. 6.

Figure 13:
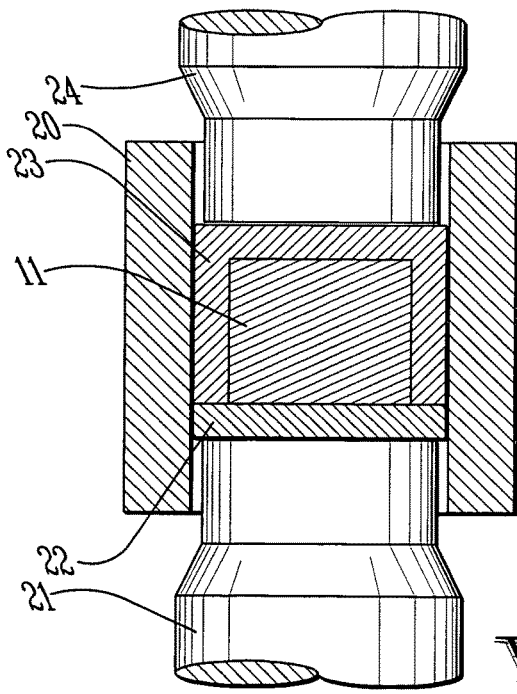
FIG. 13 is an elevation view of a die apparatus for forming the tablet of the present invention using a powder coating technique. The tablet and tool for holding the tablet are shown in cross-section.

A suitable technique to manufacture the tablet 10 of the present invention is known as dry powder coating. In this technique as shown in FIG. 13, a core 11 would first be formed using techniques known in the art. A tool 20, shown in cross-section in FIG. 13, having the desired cross-sectional shape would be placed on a lower die 21. The interior of the tool 20 is then filled with a first layer 22 of a powder to form the coating for the first region 14. The core 11 is then placed on the first layer 22 of powder. The remaining space in the tool 20 around and above the core 11 is then filled with a second layer 23 of powder to form the second region 15 of the coating. An upper die 24 is then used to compress the powders around the core 11 into the asymmetrical coating for the tablet 10. Modifications to this process may be used to produce varied embodiments of the present invention.

The present invention uses asymmetrically coated tablets so that immediate release or time-delayed release times can be precisely controlled and the extended release tablet may provide zero-order or first-order extended release and pulsatile release depending on the excipients used in the tablet formulations. Immediate release or time-delayed release time can be precisely determined. Extended release kinetics can be manipulated as a dosage form designer wishes.

The present invention has been described with reference to certain preferred and alternative embodiments that are intended to be exemplary only and not limiting to the full scope of the present invention as set forth in the appended claims. For example, various combinations of the embodiments described can be employed to design a dosage form for whatever release kinetics are desired. Further, although the embodiments described above relate to a dosage form having zero-order kinetics, the present invention is not so limited.

What is claimed is:

1. An asymmetrically coated tablet for extended release of a drug, comprising:
   a core comprising a drug dispersed throughout said core in at least one excipient; and
   a coating covering said core, wherein said coating comprises a first region and a second region, wherein said first region of said coating and said second region of said coating do not comprise a drug,
   wherein said core comprises a cross-sectional area that is constant along an entirety of a longitudinal length of said core such that the rate of release of said drug from said core is constant under conditions effective to dissolve said core,
   wherein said first region coats a portion of said core such that dissolution of said first region exposes said constant cross-sectional area of said core and said second region coats a remaining portion of said core.

2. The tablet of claim 1, wherein said first region comprises a water soluble polymer and said second region comprises a water insoluble polymer.

3. The tablet of claim 1, wherein said first region and said second region comprise water soluble polymers and wherein said first region has a rate of dissolution greater than a rate of dissolution of said second region.

4. The tablet of claim 1, wherein said first region comprises an enteric polymer.

5. An asymmetrically coated tablet for extended release of a drug, comprising:
   a core comprising a drug dispersed throughout said core in at least one excipient; and
   a coating covering said core, said coating comprising a first region formed about said core by compression of a first layer of a first dry powder and a second region formed about said core by compression of a second layer of a second dry powder;
   wherein said first region of said coating and said second region of said coating do not comprise a drug;
   wherein said core comprises a cross-sectional area that is constant along an entirety of a longitudinal length of said core such that the rate of release of said drug from said core is constant under conditions effective to dissolve said core;
   wherein said first region of said coating coats a portion of said core such that dissolution of said first region exposes said constant cross-sectional area of said core and said second region of said coating coats a remaining portion of said core.

6. The tablet of claim 5, wherein said first region and said second region comprise water soluble polymers and wherein said first region has a rate of dissolution greater than a rate of dissolution of said second region.

7. The tablet of claim 5, wherein said core comprises a first part and a second part.

8. The tablet of claim 5, wherein said core comprises a water insoluble polymer.

9. The tablet of claim 5, wherein said first region comprises an enteric polymer.

10. A method of making an asymmetrically coated tablet comprising:
    obtaining a tablet core comprising a drug dispersed throughout said core in at least one excipient;
    placing the core on a first layer of powder;
    covering the core with a second layer of powder; and
    compressing the powders around the core to form a tablet having a coating covering the core;
    wherein the coating comprises a first region and a second region,
    wherein the first layer of powder forms the first region and the second layer of powder forms the second region;
    wherein said first region of said coating and said second region of said coating do not comprise a drug;
    wherein said core comprises a cross-sectional area that is constant along an entirety of a longitudinal length of said core such that the rate of release of said drug from said core is constant under conditions effective to dissolve said core;
    wherein said first region of said coating coats a portion of said core such that dissolution of said first region exposes said constant cross-sectional area of said core and said second region of said coating coats a remaining portion of said core.

11. The method of claim 10, wherein said first region and said second region comprise water soluble polymers and wherein said first region has a rate of dissolution greater than a rate of dissolution of said second region.

12. The method of claim 10, wherein said core comprises a first part and a second part.

13. The method of claim 10, wherein said core comprises a water insoluble polymer.

14. The method of claim 10, wherein said first region comprises an enteric polymer.

* * * * *

UNITED STATES PATENT AND TRADEMARK OFFICE
CERTIFICATE OF CORRECTION

PATENT NO. : 10,071,060 B2
APPLICATION NO. : 11/443666
DATED : September 11, 2018
INVENTOR(S) : Cherng-ju Kim Page 1 of 1

It is certified that error appears in the above-identified patent and that said Letters Patent is hereby corrected as shown below:

In the title, "Asymmetrically Coated Table" should be changed to --Asymmetrically Coated Tablet--.

Signed and Sealed this
Fourth Day of December, 2018

Andrei Iancu
*Director of the United States Patent and Trademark Office*